United States Patent
Grold et al.

(10) Patent No.: US 7,355,519 B2
(45) Date of Patent: Apr. 8, 2008

(54) BODY FORCE ALARMING APPARATUS AND METHOD

(75) Inventors: Kevin Grold, 2923 Sandy Point, #6, Del Mar, CA (US) 92014; Adrian Pelkus, San Marcos, CA (US); Michael P. Eddy, Del Mar, CA (US)

(73) Assignee: Kevin Grold, Del Mar, CA (US)

( * ) Notice: Subject to any disclaimer, the term of this patent is extended or adjusted under 35 U.S.C. 154(b) by 341 days.

(21) Appl. No.: 10/708,304

(22) Filed: Feb. 24, 2004

(65) Prior Publication Data

US 2005/0184878 A1  Aug. 25, 2005

(51) Int. Cl.
*G08B 23/00* (2006.01)

(52) U.S. Cl. ............... 340/573.7; 340/665; 340/573.1; 482/74; 482/79; 36/1; 600/587

(58) Field of Classification Search ............. 340/573.7
See application file for complete search history.

(56) References Cited

U.S. PATENT DOCUMENTS

| | | | |
|---|---|---|---|
| 4,426,884 A * | 1/1984 | Polchaninoff ................. 73/172 |
| 4,647,918 A * | 3/1987 | Goforth .................... 340/573.1 |
| 5,107,854 A | 4/1992 | Knotts et al. |
| 5,253,654 A | 10/1993 | Thomas et al. |
| 5,269,081 A | 12/1993 | Gray |
| 5,323,650 A * | 6/1994 | Fullen et al. ............. 340/573.1 |
| 5,357,696 A | 10/1994 | Gray et al. |
| 5,511,561 A | 4/1996 | Wanderman et al. |
| 5,619,187 A | 4/1997 | Schmidt et al. |
| 5,813,142 A * | 9/1998 | Demon ........................... 36/29 |
| 5,929,332 A * | 7/1999 | Brown .......................... 73/172 |
| 6,087,926 A | 7/2000 | Hajianpour |
| 6,122,846 A | 9/2000 | Gray et al. |
| 6,174,294 B1 | 1/2001 | Crabb et al. |
| 6,219,625 B1 * | 4/2001 | Singh .......................... 702/160 |
| 6,272,863 B1 | 8/2001 | Pfefferle et al. |
| 6,273,863 B1 * | 8/2001 | Avni et al. ................... 600/587 |
| 6,278,378 B1 | 8/2001 | Feiner et al. |
| 6,405,606 B1 * | 6/2002 | Walczyk et al. ........ 73/862.381 |
| 6,752,028 B2 * | 6/2004 | Bechmann ............. 73/862.391 |
| 2002/0093428 A1 | 7/2002 | Bechmann |

* cited by examiner

*Primary Examiner*—Benjamin C. Lee
*Assistant Examiner*—Eric M. Blount
(74) *Attorney, Agent, or Firm*—Michael P. Eddy

(57) ABSTRACT

A device and method to detect force and provide feedback to a runner or jogger so that the person can judge whether to adjust his or her stride in order to lessen the impact on his or her body. The device includes a housing, a power supply, a piezo sensor, a controller, and an output generator. The piezo sensor is accommodated within a user's shoe and is connected to the controller, and the controller, output generator and power supply are accommodated within the housing. The controller is connected to the output generator so that it is set to generate a signal to the output generator when a threshold level of force signal is received from the piezo sensor. The sensor signals the controller when force from an impact is applied to the piezo sensor and the controller signals the output generator when one or more signals indicating threshold levels of force have been reached, and the output generator generates a perceivable signal in response to the controller's one or more signals.

4 Claims, 4 Drawing Sheets

BODY FORCE ALARMING APPARATUS AND METHOD

BACKGROUND OF INVENTION

Force detection devices have been commonly used in the prior art for rehabilitation from injuries caused by trauma to lower limbs. A large percentage of joggers and runners become injured in some fashion while running. Most of these joggers and runners do not realize that an improper stride may directly lead to, or at a minimum, contribute to these injuries. Overstriding is one example of an improper stride used by runners. Webster's dictionary defines overstride as "to stride over or beyond." Overstriding most often occurs when a moving person's foot strikes the ground in a position in front of a point directly below the runner's center of gravity. In this situation, the center of gravity is located just above the center of the pelvis when that person is running, and when a runner's foot strikes the ground too far in front of the center of gravity, the foot acts to brake or slow down the runner's momentum. The foot can land on the ground in a propping or braking position. When this happens, the foot's impact retards the forward motion of the body, and additional energy must be then expended to compensate for the loss.

A typical foot strike creates large impact forces which are mostly absorbed by the body's muscles, tendons, and ligaments. Any misalignment or imbalance in the gait can turn into a problem due to the repetition of the movements in walking, jogging or running. Most joggers and runners are unaware of these misalignments or imbalances, and of the loss of forward motion associated with inefficient strides, and many can spend an entire lifetime of running or jogging without knowing how much more economical their running or jogging action would be if they learned to adjust to a more efficient stride. For example, some runners may need to reduce their overall stride length and pick up their cadence to achieve the desired strides in their gait.

Misalignment caused by overpronation in the leg can also lead to a whole host of injuries in areas higher in the limbs such as the knees and hip joints. Excessive supination, or the outward rolling of the foot, is not as common but can lead to similar debilitating effects over a period of time. Lack of any pronation can lead to excessive force being distributed throughout the body as the foot is not able to absorb the impact force. Some examples of typical injuries related to running and jogging are: achilles tendinitis, arthritis of the foot and ankle, ankle pain, arch pain, back pain, bunions, calf strain, clubfoot, corns, fractures of the heel, groin pull, hammertoes, hamstring pain, heel pain, hip pain, iliotibial band syndrome, knee pain (or runners knee), morton's neuroma (persistent pain in the ball of your foot), neck & shoulder pain, overpronation, shinsplints, side stitches, sprained ankle, stress fractures of the foot and ankle, thighbone fracture, toe and forefoot fractures. All of the aforementioned maladies can be caused or exacerbated by an inefficient running stride.

Unlike the present invention, variations of devices known in the prior art use resistive sensors which are designed to change resistance when a force or weight is applied, in essence measuring the weight applied to the surface of the resistor. Also, many of these devices in the prior art are large, bulky and expensive, and they are primarily used in controlled settings to analyze gait analysis. These known devices were created for patients who had been injured and were in the process of rehabilitation. The machines were specifically designed to monitor the amount of weight or pressure applied to the leg while the injured person was recovering.

Runners who have had a running related injury are frequently told to stop running so as to avoid further aggravation of their injury. Medical doctors will also frequently prescribe anti-inflammatory medication in addition to rest. During aerobic activity, the cushioning found in an athletic shoe can only do so much to help when the athlete has an improper stride such as a pounding stride. A bad stride can not only slow a runner down, bouncing, hopping, and pounding when running wastes energy and places enormous amounts of strain on their ankles, knees, hips, back and neck. The present invention gives the athlete the ability to moderate his or her stride to prevent this strain and energy waste.

In general, all running effort should be directed forward. There should be very little up and down motion. Runners who bounce or hop when they run are wasting energy. They are also putting excessive stress on the knees, hip and back along with their whole body.

SUMMARY OF INVENTION

The present invention relates generally to force detection in limbs, and more specifically to a device and method to provide feedback to a runner or jogger so that the person can judge whether to adjust his or her stride in order to lessen the impact on the body.

The apparatus includes a body force alarming apparatus comprising a housing, a power supply, a piezo sensor, a controller, and an output generator, wherein said piezo sensor is accommodated within a user's shoe and connected to said controller, wherein said piezo sensor, controller and said output generator are connected to said power supply, wherein said controller, output generator and power supply are accommodated within said housing, wherein said controller is connected to said output generator, wherein said controller is set to generate a signal to the output generator when a threshold level of force signal is received from said piezo sensor, wherein said sensor signals said controller when force from an impact is applied to said piezo sensor, wherein said controller signals said output generator when one or more signals indicating threshold levels of force have been reached, and wherein said output generator generates a perceivable signal in response to a signal from said controller.

An embodiment of the body force alarming apparatus includes two or more piezo sensors to provide feedback when one or more levels of force are sensed instead of one. Another embodiment includes a means to automatically adjust the controller. Another embodiment of the present invention includes a microcontroller wherein said microcontroller, once activated by a user with a switch, performs the steps of recording one or more impact levels for a predetermined period of time, averaging said amounts of impact recorded over said period of time; and setting the controller's feedback threshold to an amount above, equal to, or below the average value. Yet another embodiment includes a microcontroller wherein said microcontroller, once activated by a user with a switch, performs the steps of recording one or more impact levels for a predetermined period of time, averaging said amounts of impact recorded over said period of time; and setting the controller's feedback threshold to an amount greater than said average.

Another embodiment of the body force alarming apparatus includes an output generator with a separate power source wherein the controller and output generator are wirelessly connected. Other embodiments of the body force alarming apparatus include one that has an output generator that is attached separately to the body of the user, another that has a controller attached separately to the body of the user, another that has an output generator separated from the user, and another that has the controller is separated from the user.

Yet another embodiment of the body force alarming apparatus includes an impact transducer. Another embodiment of the body force alarming apparatus includes the sensor, controller and feedback generator accommodated within a person's shoe. Another embodiment of the body force alarming apparatus includes a perceivable signal that is an audio beep, a musical tone or tones, a click, a vibration, a shock, a pressure applied to the user, or a light emission.

Another embodiment of the body force alarming apparatus includes a controller that is preset to generate two or more signals to the output generator when two or more corresponding signals are received from said sensor which are at or above the two or more corresponding threshold levels of force. Another embodiment of the body force alarming apparatus includes an output generator that generates two or more corresponding perceivable distinctly different signals in response to each corresponding signal from said controller. And another embodiment of the body force alarming apparatus includes a low battery sensor wherein a low battery alarm is produced when a low battery is detected. Another embodiment of the body force alarming apparatus includes an on/off switch. Another embodiment of the body force alarming apparatus includes a digital display for displaying one or more amounts of force applied to the sensor. Another embodiment of the body force alarming apparatus includes a beginner setting, an intermediate setting, and an advanced setting, wherein when the controller is set to beginner, intermediate or advanced and the corresponding threshold is set to take a large, medium or small impact for the controller to signal the output generator. Another embodiment of the body force alarming apparatus further includes a wireless receiver to remotely receive output data transmitted by the controller. Another embodiment of the body force alarming apparatus further includes a wireless receiver to remotely receive output data transmitted by the sensor. And another embodiment of the body force alarming apparatus further includes a wireless receiver to remotely receive output data transmitted by the output generator. The output data can then be recorded.

Methods of the present invention comprise the steps of setting the controller to generate a signal to the output generator when a threshold level of force signal is received from a piezo sensor, signaling said controller with the sensor when an amount of force from an impact is applied to said sensor, signaling an output generator when one or more signals from said sensor indicate that one or more predetermined threshold levels of force have been sensed, and generating a perceivable signal with said output generator in response to a signal from said controller using one or more of the aforementioned apparatuses.

To the accomplishment of the above and related objects, this invention may be embodied in the form illustrated in the accompanying drawings, with attention being called to the fact that the drawings are illustrative only and that changes may be made in the specific constructions illustrated and describes within the scope of the appended claimed subject matter.

BRIEF DESCRIPTION OF DRAWINGS

The above and other objects, advantages and features of the present invention will be more readily apparent from the following description, when read in conjunction with the accompanying drawings wherein.

DETAILED DESCRIPTION

Figure 1:
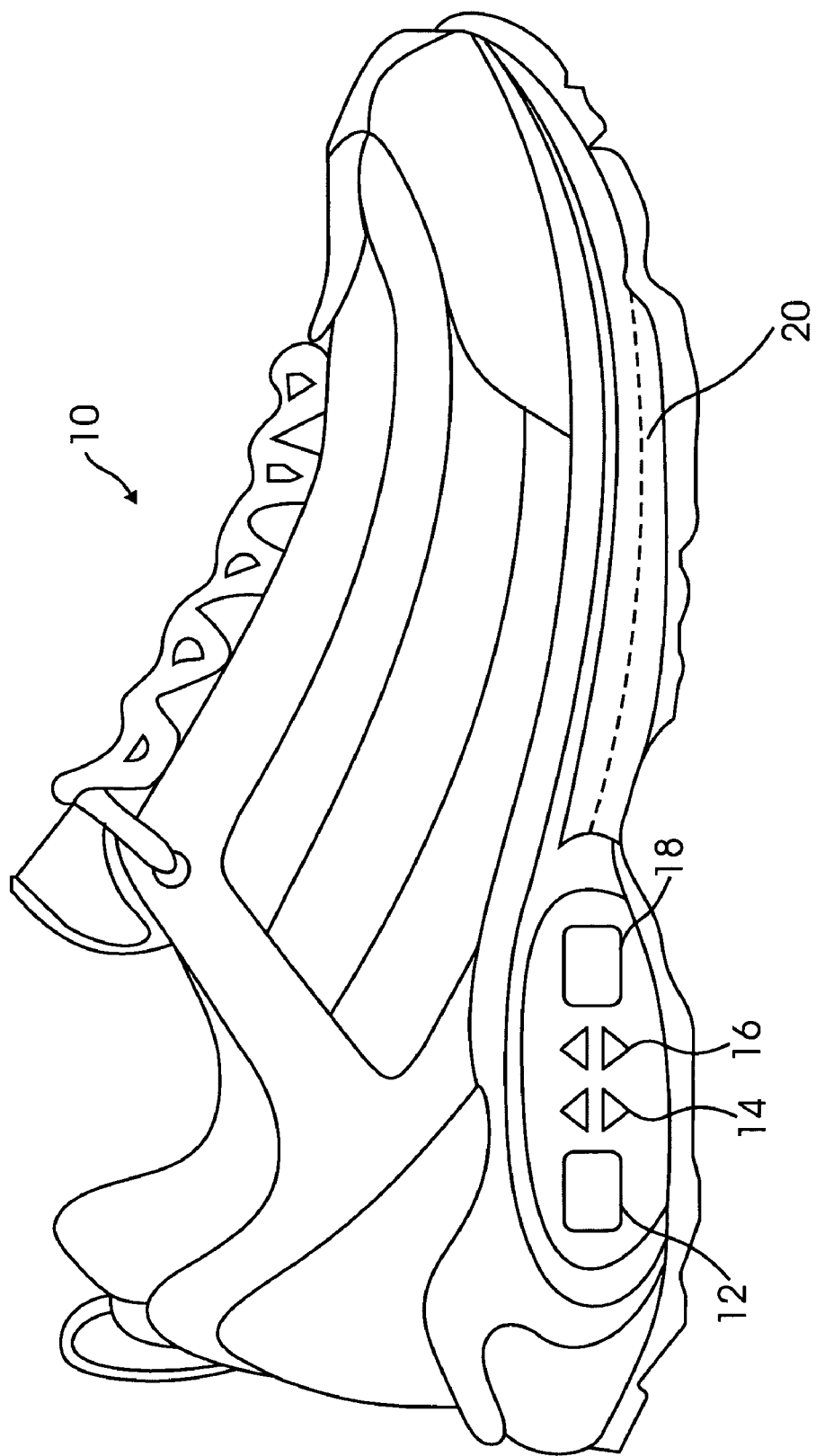
FIG. 1 is a perspective view of an embodiment of the claimed subject matter.

Embodiments of the present invention can be used by both amateur and professional athletes alike to improve their performance by using the apparatus and method to understand the forces placed on their bodies while they are in motion. Other potential users of the present invention include rehabilitation patients, such as amputee patients optimizing the use of their prosthetic limb, and patients undergoing limb-salvage procedures who need help developing efficient walking strides. Finally animal trainers can use embodiments of the present invention to monitor forces on limbs of animals in training or rehabilitation.

The present invention makes use of lightweight technology which allows the whole system to be self-contained and thus not constrained to a controlled environment such as a laboratory. Unlike prior inventions which need to be programmed with bulky equipment, this invention also allows the runner to self-adjust the threshold levels and thus create a smoother, less injurious stride while running outside in a natural environment. On the technical side, prior inventions use resistive sensors which change resistance when a force or weight is applied because they are designed to measure weight while this present invention utilizes the latest technology with a single sensor or with multiple sensors, that can directly transduce impact or shock into a proportional output voltage to measure the impact on a runner's body. The use of such a self-contained digital system can alleviate the need for a digital signal conditioning systems found in previous inventions.

Piezo technology, based on physical contact and elastic coupling, is used in the embodiments of the present invention. Piezo actuators are used in the present invention as transducers to covert energy in the form of stress from the foot as it impacts a surface, into an electronic signal. For example, the impact can be the force or impetus transmitted by the collision of the foot with the ground.

When a piezoceramic element is mechanically stressed by force, it generates an electric charge. This charge is used in several embodiments to signal the output generator to generate a signal, such as an audio alarm, when the force reaches a predetermined threshold. Other suitable transducers are devices which convert pressure energy from the energy of the impact to an electronic signal.

Piezo actuators are preferable because they take much less power to operate than solenoids, which is particularly beneficial in applications such as this where power consumption is an issue. Piezo actuators not only have a low level of power consumption, they have high reliability and environmental ruggedness. A piezo device is suitable to measure transient force measurements lasting less than 0.1 second. This force that is measured is force applied to the body, or the entire material or physical structure of an organism, specifically of a human or animal.

In one embodiment, a sheet of piezoceramic sheet stock is cut into a size that will fit in the insole of a user's shoe with a diamond saw or by using a razor blade and a straight edge to score to score the piezo surface and then making a controlled break. Any type of Piezo generators or sensors, such as single layer, 2-layer and multi layer generators, may be employed.

Lead wires are either already connected to the piezo sensors as purchased or they are connected after the product is cut. The piezo sensor is connected by a wire to controller which is designed to receive and evaluate the signals from the sensor. The sensor in one embodiment is placed inside a user's shoe, under the sole of the foot. The sensor can be placed within a user's shoe, for example it can be contained in a user's insole, midsole, or it can be placed within other areas of the shoe. It can also be affixed with adhesive to a portion of an insole, midsole or the shoe itself. It can also be placed anywhere on the body to measure impact at that point on the body.

The output from the piezo strain sensor is fed into the controller (which can be anything from a simple circuit to an elaborate Digital Signal Processing computer) which in turn processes the input from the sensor and sends a signal to an output generator when appropriate, and in doing so, the controller acts to regulate the apparatus and method. The controller is accommodated within a housing 12 which also accommodates a power supply, typically a slim or coin sized battery. The housing can be made of materials such as plastic, fabric or any other suitable medium, or it can be integrated into the shoe or limb attachment.

Figure 2:
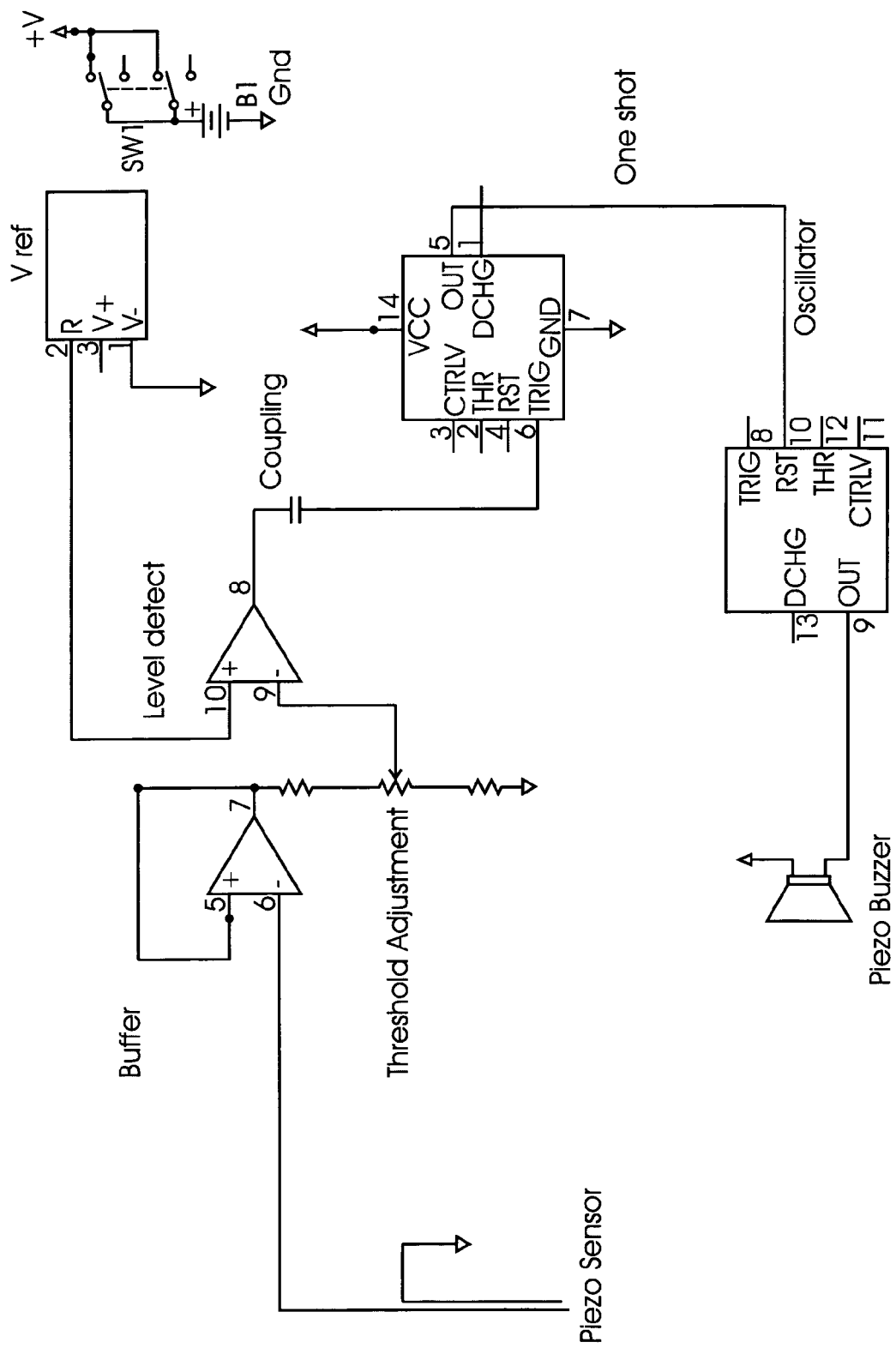
FIG. 2 is a block diagram of circuits used in an embodiment of the claimed subject matter.

The sensor is attached to the controller which selectively sends signals to the output generator which generates sounds or other perceptible signals to the user. A circuit diagram of the controller is illustrated in FIG. 2. One function of the controller is to check, adjust, or determine by comparison with a preset amount, the force level sensed by the sensor. Another function is to generate one or more signals to the output generator. The output generator recognizes the one or more signals and generates perceivable output to the user. The perceivable output can be adjustable and can vary with the one or more signals generated with the controller. For example, the output generator can generate a high tone with one impact threshold and a low tone with the base threshold or it can generate a signal tone when the one set threshold is reached.

Before the embodiments of the present invention are initially used, they are pre-set to generate output when at least one specific amount of force is sensed by the controller. In later steps, the controller is set to generate a signal to the output generator when a threshold level of force signal is received from said sensor. This is initially set before the first use to produce an output signal when a certain amount of impact force is sensed, and this amount is approximately 50 percent of a two hundred pound human's weight. This can be changed at any time before or after the initial use based on the user's preferences.

The auto adjusting features of other embodiments can be used in different ways with the main goal which is to allow auto adjusting of the controller so that the level of desired feedback is set automatically to the user's preference. The threshold levels can be auto adjusted to various levels depending on level of feedback desired and the amount of impact generated by the user.

In one embodiment, a runner can run with his or her normal stride to calibrate the base threshold level. The controller can be set to "learn mode" or "auto-calibrate mode" from a user originated action such as pressing a "calibrate mode" button found on the outside of the housing 12. Controller, now in learn mode, can receive and record the impact force levels from the sensor over a predetermined period of time, approximately 20 seconds, or until learned mode is turned off by the user with a second pressing of the "calibrate mode" button or until the time has run out.

After the "learn mode" is completed, the controller determines the threshold level 100 based on the average impact force levels recorded during the learn mode function. The controller then stores this threshold level 100 into the controller's internal memory, where it can then be used in conjunction with determining whether or not to produce a signal to the output generator. The learn mode results can be stored as threshold level 100 or, in an alternative embodiment, the learn mode results can be changed to add or subtract a percentage before they are stored as threshold level 100. The threshold level 100 can also be changed after the learn mode results have been stored as threshold level 100. For example, a runner uses the auto adjust learn mode to adjust the controller to his or her preference, and the controller can add 10 percent so that if the runner goes over his or her preference by more than 10% impact, the controller will generate a signal to the output generator and a perceivable signal will be heard by the runner.

Another embodiment or variation has an additional user determined setting for beginner, intermediate and advanced users, in the form of a switch. This setting varies the average threshold which was derived from the learn mode. The beginning level has the highest level of threshold, the intermediate level has a middle level of threshold and the advanced level has the lowest threshold before the output generator is signaled by the controller.

For example, if the controller is set to beginner, the threshold is very high and it takes a large impact for the controller to signal the output generator which in turn generates a signal to the user that is perceivable. The beginner could have a somewhat impactful stride and still not generate a signal to the output generator until a strong impact stride was detected by the controller.

Embodiments of the present invention are applicable in use with humans and animals alike. Embodiments of the present invention will allow runners and doctors another option with their rehabilitation plans and allow runners to get back to what they love more quickly and safely. In animal uses, one embodiment is used to keep track of the levels of impact on the limbs of a horse that exceed a specified threshold. In this manner, the horse trainer can monitor the overall impacts to the limbs of the horse, especially in cases of rehabilitation when reduction of force is necessary for the recovery on an injured limb or knee.

Embodiments of the present invention reduce impact on your body by alerting with an alarm, for example a loud beep, when the user is impacting the ground with a harmful or inefficient stride. In this way, runners can monitor their strides while at the same time avoid potential injuries by moving using safer strides. This results in less stress to the entire body. In one embodiment, a runner can set his or her running skill level before they begin to run. In this way, a beginner can use a more forgiving setting than a setting used by a highly skilled runner. This embodiment alerts the user with a beep whenever a set threshold is reached, and this beep serves to notify the runner and/or the trainer to run with strides that have less impact and thus more efficiently. Further, the challenge of perfecting one's stride can be entertaining to the user and further serve as a distraction to the runner during times of prolonged activity. In another example of a use for an embodiment of the present invention, when a runner is receiving information that she or he is impacting harder than she or he would like, and the runner is unable to modify their running stride to create ground strikes with less impact, the runner can instead move to a more forgiving surface, such as a running track or a sandy beach. The present invention helps athletes run longer, and it helps them more run more frequently because it helps prevent injuries.

Diagrams and/or instructions showing examples of proper strides and one or more exemplary impact levels based on various skill levels, such as a beginner, intermediate or expert, can be included with or provided in conjunction with the present embodiments. Similarly, one or more training programs can be implemented which are directed to the requirements of specific athletic goals or athletic fields such as soccer or track. These training programs, diagrams and instructions can be further customized for various types of athletic shoes.

Output received from the controller, for instance data that is representative of impact levels and/or user settings or output send directly from the sensor in raw or translated form, can be displayed inside a clear housing or outside the housing. The display can be connected directly via a wire or the information can be sent wirelessly by one or more components of the present invention, such as the controller, to a remote receiver. In one embodiment, the controller transmits to a remote receiver the impact levels in numerical format as the impact information is received by the controller. Numerical values, for example approximating impact levels, can be displayed in a range from one to ninety nine as they occur in real time.

The numerical format used in relation to impact levels can be based on a scale such as previously described (where numbers from zero to ninety nine are used to approximately equal the range of impact sensed from the least amount to most amount) or it can be based on a percentage of a maximum impact level sensed. The maximum impact level can by set by the user, preset to an arbitrary level, or it can be the maximum impact that can be sensed by the sensor. This output can also be used to compare results with previous results or with previously stored results found in average runners for a particular body style or a body measurement such as weight. The output data can also be compared either post-race or real time to other data gathered from various sources such as competitors in the same race, or they can be compared to past results of the same athlete or others, or even compared to hypothetical goals or standards. Even other embodiments can compare the recorded or real time data with stored impact levels of famous runners or athletes. In other embodiments, real time or delayed impact levels can be provided to broadcast television viewers, for instance using impact levels of famous runner while they are participating in running events.

In another embodiment, the controller or the output generator is capable of sending output data wirelessly to a remote recorder or a computer system where the data is able to be compiled or assimilated for further use. These uses include comparing the data to historical data, such as previous race results, displaying real time or delayed data results to viewers on television or the computer networks, and integrating the data into other computer implemented methods. For example, the data received remotely could be displayed on a television broadcast along with the race itself, or it could be displayed on a web site so the public would be able to follow specific runners or running events.

Data from the sensor and controller can also be recorded and stored for real time by the present invention itself allowing for delayed or subsequent downloading by a computer for later use with a computer implemented method. This can be accomplished with either a wired connection or a wireless connection. Once output to a remote receiver, the data can be easily displayed on a computer or formatted for a television. The data sent by the present invention can include the setting levels used by the user, the number of alarm signals generated by the controller, maximum and minimum threshold levels, and intensity levels of the impacts sensed. In other embodiments, the output generator and controller are able to be attached individually or separately anywhere on the body. They can also be located in a location away from the impact sensor, for instance a completely separate stationary location, moving location or on another person, such as in the case of a personal trainer or an animal handler wearing the output generator, connected wirelessly to the controller, either on a wrist or wired in connection with headphones. The output generator and controller individually or together can also be part of a separate or integrated computer system.

In several embodiments specifically related to use with a running shoe, the components are not only safe and reliable, but they are long-lasting. The added weight of the components of the embodiments of the present invention add less than few ounces to the weight of the shoe. When the shoe is used as the housing, and the other components are integrated into the shoe, the weight of the embodiment of the present invention will be even less.

Other embodiments of the present invention include features such as an on/off button or an on/off switch so that the user can power on and power off the device to increase the life of the battery. In yet another embodiment, a battery save function can be implemented, for example it can be included as an additional function of the controller, which will serve to place the embodiment in a battery save mode. In this manner, the controller would initiate a power off signal after a predetermined period of time when no impact levels are sensed, for example in a five or ten minute period of time.

FIG. 1 is a perspective view of an embodiment 10 of the claimed subject matter wherein the athletic shoe serves as a housing for the embodiment 10. An audible tone or beep emitted from speaker 12 is heard by the user when a predetermined threshold is reached. Buttons 14 allow the user to increase or decrease the volume of the audio output emitted from speaker 12. Buttons 16 allow the user to manually increase or decrease, using the corresponding up and down arrows, the threshold level of the embodiment. In this manner, the user can use the up arrow to raise the threshold level and the down arrow to decrease the threshold level. When the threshold level is increased, more impact is needed for the embodiment to alarm. Similarly, when the threshold level is decreased, less impact is needed for the embodiment to alarm.

FIG. 1 also shows display 18 with a value of "64" indicating the level of the current or recent impact. In this embodiment, the number displayed is scaled in direct proportion to the impact level, with no impact displaying zero and the greatest sensed impact, within the maximum limit of the sensor, being ninety nine. Sensor 20's position, which would not be externally visible to the user, is indicated by the dashed line. In this embodiment, it is incorporated into the sole of the shoe.

Figure 3:
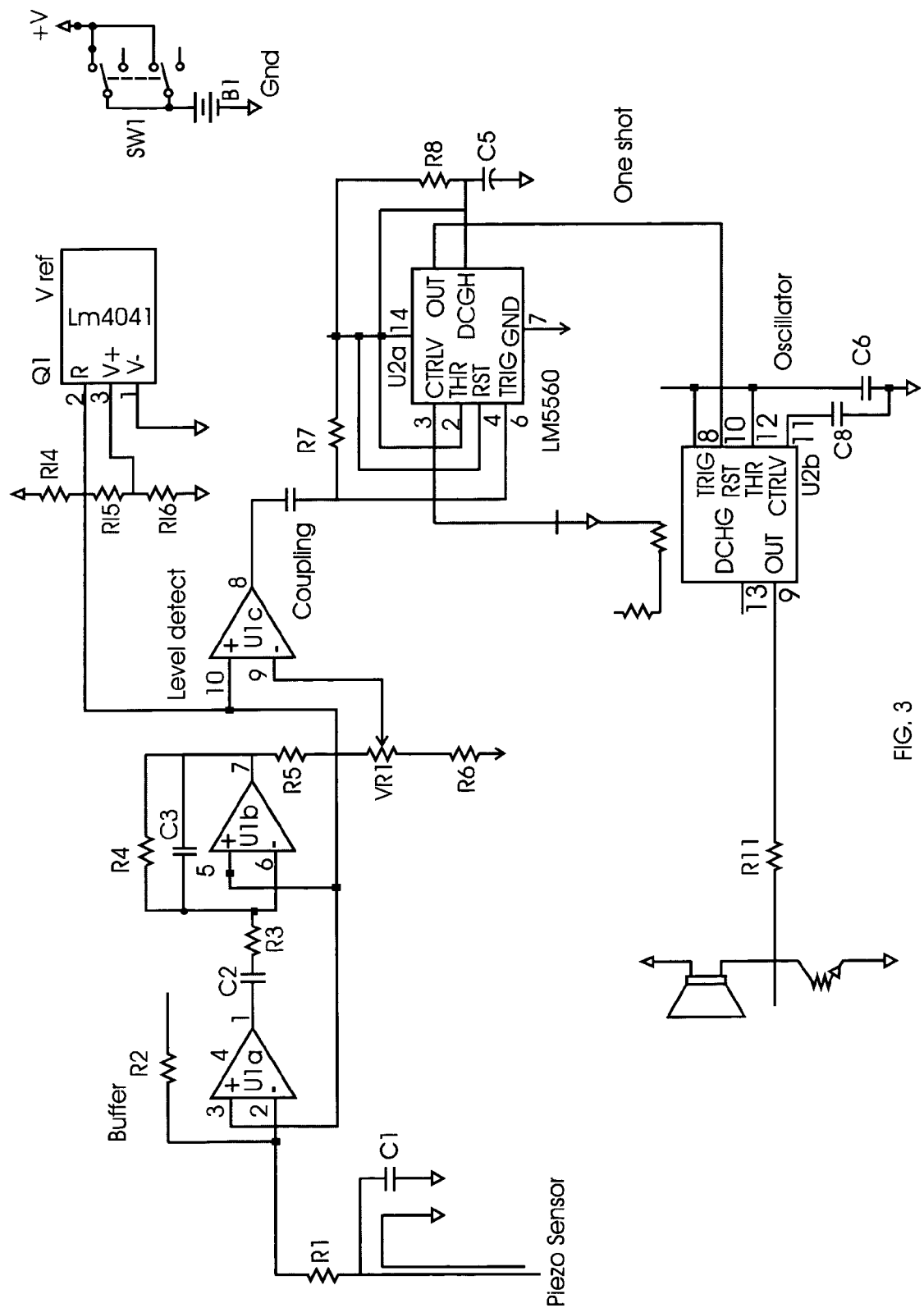
FIG. 3 is a circuit diagram of an embodiment of the claimed subject matter.

FIG. 2 is a block diagram of the circuits used in an embodiment of the claimed subject matter. FIG. 3 is a more detailed circuit diagram of the embodiment shown in FIG. 2.

Figure 4:
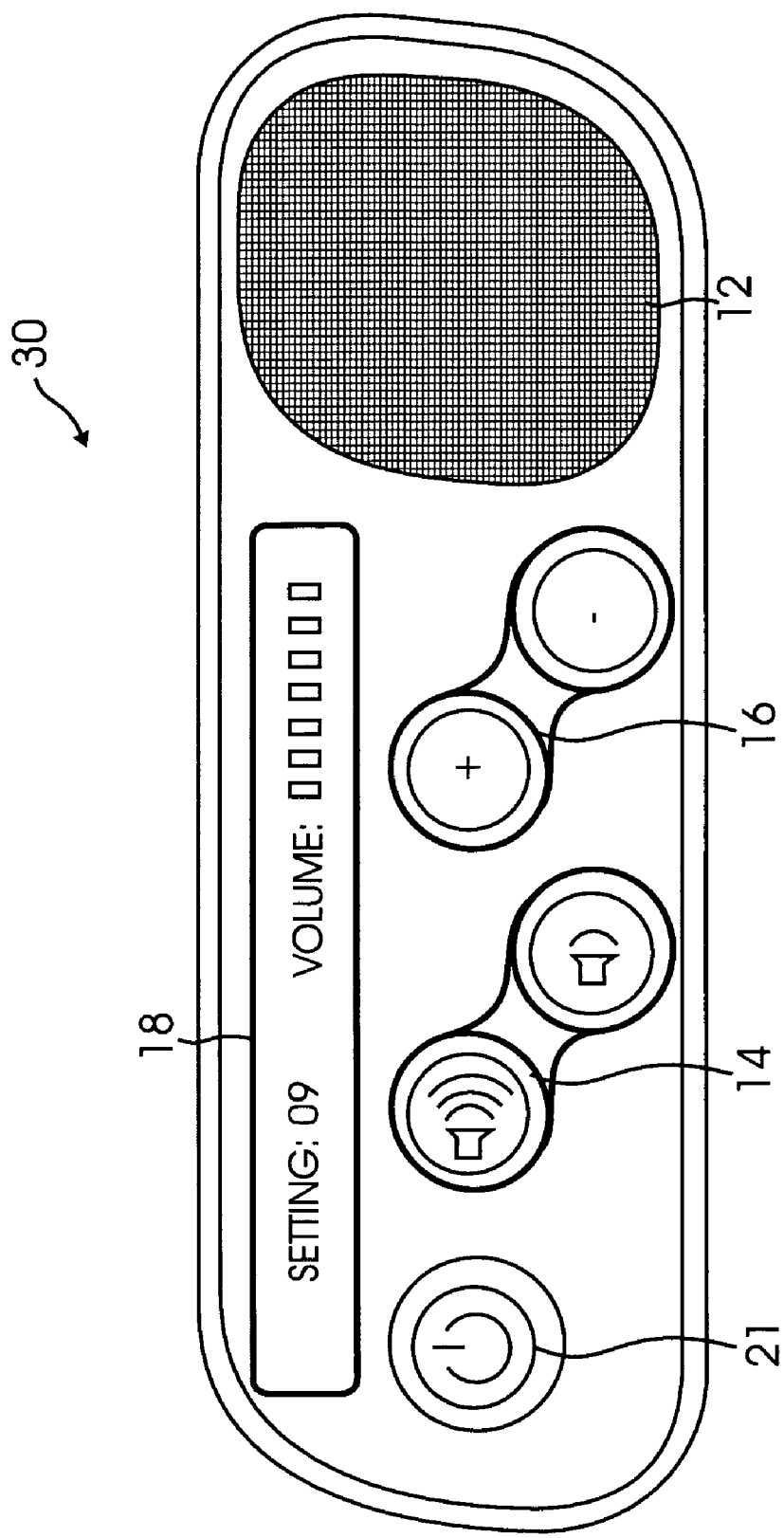
FIG. 4 is a perspective view of a control panel of an embodiment of the claimed subject matter.

FIG. 4 is an alternative user interface 30 which can be used in conjunction with an athletic shoe. This embodiment includes an on/off switch 21, a display 18 showing the current threshold level setting as well as the volume, a pair of volume setting buttons 14, threshold adjustment buttons 16, and a speaker 12.

While the present invention has been illustrated and described by means of specific embodiments and alternatives, it is to be understood that numerous changes and modifications can be made without departing from the spirit and scope of the invention. Therefore, it should be understood that the invention is not to be limited in any way except in accordance with the appended claims and their equivalents.

The invention claimed is:

1. A body force alarming apparatus for warning of excessive impact on a user to prevent injuries comprising:
   a housing;
   a power supply;
   a piezo sensor;
   a controller;
   an output generator; and
   a microcontroller;
   wherein said piezo sensor is accommodated within a user's shoe and connected to said controller;
   wherein said piezo sensor, controller and said output generator are connected to said power supply;
   wherein said controller, output generator and power supply are accommodated within said housing;
   wherein said controller is connected to said output generator,
   wherein said controller is set to generate a signal to the output generator when a threshold level of force signal is received from said piezo sensor;
   wherein said sensor signals said controller when force from an impact is applied to said piezo sensor; and
   wherein said controller signals said output generator when one or more signals indicating threshold levels of force have been reached; and
   wherein said output generator generates a perceivable signal indicative of excessive impact in response to a signal from said controller and wherein said microcontroller, once activated by a user with a switch, performs the steps of:
   recording one or more amounts of impact for a predetermined period of time;
   averaging said amounts of impact recorded over said period of time; and
   setting the controller's feedback threshold to an amount based on the average value.

2. A body force alarming apparatus of claim 1, wherein said microcontroller, once activated by a user with a switch, performs the steps of:
   setting the controller's feedback threshold to an amount above, equal to, or below the average value.

3. A body force alarming method for warning of excessive impact on a user to prevent injuries comprising the steps of:
   setting a controller to generate a signal to an output generator when a threshold level of force signal is received from a piezo sensor;
   signaling said controller with said sensor when an amount force from an impact is applied to said sensor;
   signaling said output generator when one or more signals from said sensor indicate that one or more predetermined threshold levels of force have been sensed; and
   generating a perceivable signal indicative of excessive impact with said output generator in response to a signal from said controller wherein the steps are performed using an apparatus comprised of:
   a housing;
   a power supply;
   said piezo sensor;
   said controller;
   said output generator; and
   a microcontroller;
   wherein said piezo sensor is accommodated within a user's shoe and connected to said controller;
   wherein said piezo sensor, controller, microcontroller and said output generator are connected to said power supply;
   wherein said controller, output generator, microcontroller and power supply are accommodated within said housing; and
   wherein said controller is connected to said output generator; and
   wherein said microcontroller, once activated by a user with a switch, performs the steps of:
   recording one or more amounts of impact for a predetermined period of time;
   averaging said amounts of impact recorded over said period of time; and
   setting said controller's feedback threshold to an amount based on the average value.

4. A body force alarming apparatus of claim 3, wherein said microcontroller, once activated by a user with a switch, performs the steps of:
   setting the controller's feedback threshold to an amount above, equal to, or below the average value.

* * * * *